(12) United States Patent
Lum et al.

(10) Patent No.: US 9,295,783 B2
(45) Date of Patent: *Mar. 29, 2016

(54) SYRINGE HAVING A COLLAPSIBLE PLUNGER ROD

(71) Applicant: Becton Dickinson France, S.A.S., Le Pont-de-Claix (FR)

(72) Inventors: Chee Leong Lum, Pequannock, NJ (US); Eric Schiller, Kinnelon, NJ (US)

(73) Assignee: Becton Dickinson France, Le Pont-de-Claix (FR)

( * ) Notice: Subject to any disclaimer, the term of this patent is extended or adjusted under 35 U.S.C. 154(b) by 28 days.

This patent is subject to a terminal disclaimer.

(21) Appl. No.: 14/107,462

(22) Filed: Dec. 16, 2013

(65) Prior Publication Data
US 2014/0100546 A1    Apr. 10, 2014

Related U.S. Application Data

(63) Continuation of application No. 12/859,823, filed on Aug. 20, 2010, now Pat. No. 8,632,519.

(60) Provisional application No. 61/235,869, filed on Aug. 21, 2009, provisional application No. 61/235,848, filed on Aug. 21, 2009.

(51) Int. Cl.
*A61M 5/315* (2006.01)
*A61M 5/31* (2006.01)
*A61M 5/28* (2006.01)

(52) U.S. Cl.
CPC .......... *A61M 5/31515* (2013.01); *A61M 5/3135* (2013.01); *A61M 5/31511* (2013.01); *A61M 5/31565* (2013.01); *A61M 5/28* (2013.01); *A61M 2005/31518* (2013.01); *A61M 2205/583* (2013.01)

(58) Field of Classification Search
CPC ............... A61M 5/31515; A61M 2005/31518; A61M 5/3135
See application file for complete search history.

(56) References Cited

U.S. PATENT DOCUMENTS

| | | | |
|---|---|---|---|
| 637,405 | A | 11/1899 | Papendell |
| 1,678,991 | A | 7/1928 | Marschalek |
| 2,185,536 | A | 1/1940 | Borland et al. |
| 2,347,179 | A | 4/1944 | Gorman |
| 2,946,331 | A | 7/1960 | Jungst et al. |
| 3,040,744 | A | 6/1962 | Hoggard |

(Continued)

FOREIGN PATENT DOCUMENTS

| | | |
|---|---|---|
| EP | 1323450 A1 | 7/2003 |
| WO | 9729798 A1 | 8/1997 |

*Primary Examiner* — Shefali Patel
(74) *Attorney, Agent, or Firm* — The Webb Law Firm

(57) ABSTRACT

A syringe assembly includes a syringe barrel having an exterior surface, an inside surface defining a chamber, an open proximal end, a distal end, and an outlet disposed adjacent the distal end in fluid communication with the chamber; and a plunger assembly disposed at least partially within the syringe barrel. The plunger assembly includes an elongated plunger rod and a plunger head. The elongated plunger rod is associated with the plunger head to move the plunger head within the chamber of the syringe barrel through an injection cycle. The plunger rod is adapted to move from a collapsed position extending alongside the exterior surface of the syringe barrel to an extended position engaging the plunger head to move the plunger head through the injection cycle.

12 Claims, 15 Drawing Sheets

(56) References Cited

U.S. PATENT DOCUMENTS

| | | |
|---|---|---|
| 3,045,673 A | 7/1962 | Hein |
| 3,115,135 A | 12/1963 | Sarnoff |
| 3,144,178 A | 8/1964 | Sarnoff |
| 3,730,389 A | 5/1973 | Harris, Sr. et al. |
| 4,414,983 A | 11/1983 | Evans et al. |
| 4,563,178 A | 1/1986 | Santeramo |
| 4,581,023 A * | 4/1986 | Kuntz ............... A61M 5/24 604/234 |
| 4,636,202 A | 1/1987 | Lowin et al. |
| 6,020,196 A | 2/2000 | Hu et al. |
| 6,059,756 A | 5/2000 | Yeh |
| 6,368,308 B1 | 4/2002 | Nerney |
| 2004/0116875 A1 | 6/2004 | Fischer et al. |
| 2006/0229568 A1 | 10/2006 | Koopman |
| 2007/0219506 A1 * | 9/2007 | Andersson ............... A61M 5/24 604/207 |

* cited by examiner

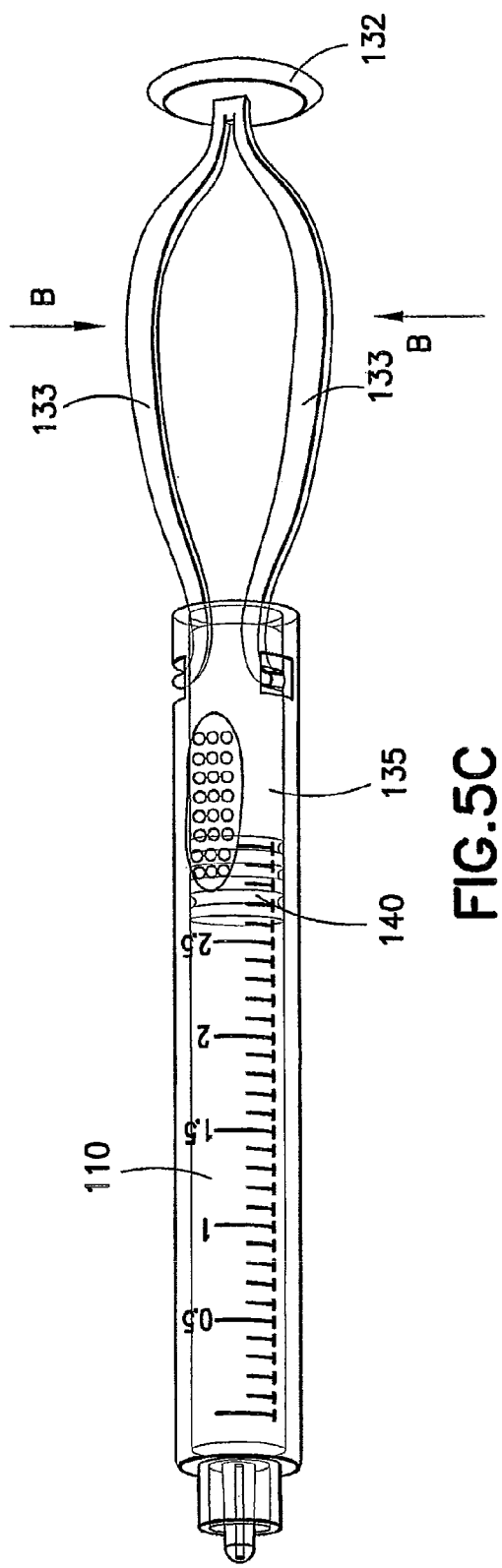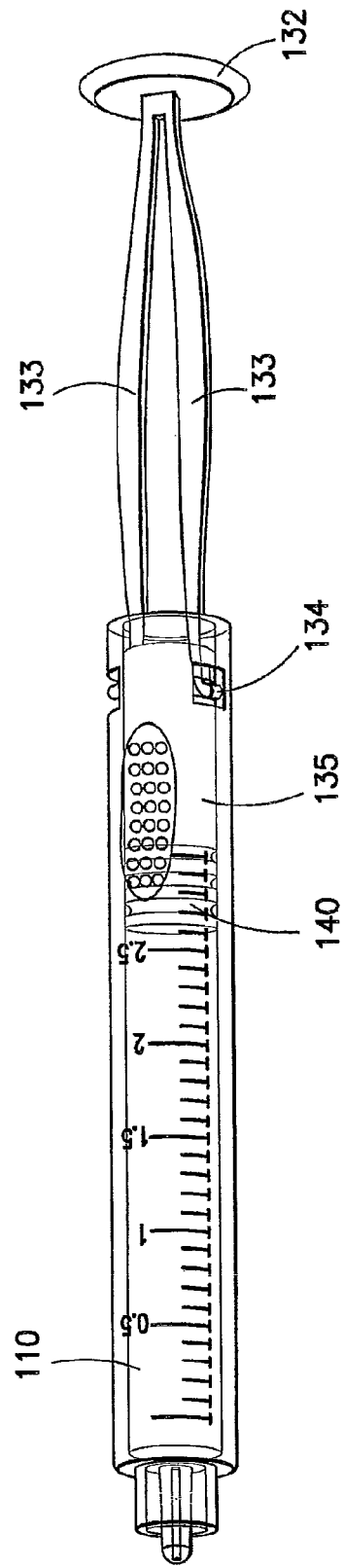
FIG.5C
FIG.5D

SYRINGE HAVING A COLLAPSIBLE PLUNGER ROD

CROSS REFERENCE TO RELATED APPLICATIONS

This application is a continuation of U.S. patent application Ser. No. 12/859,823 entitled "Syringe Having a Collapsible Plunger Rod" filed Aug. 20, 2010, which claims benefit of U.S. Provisional Patent Application Ser. Nos. 61/235,869 entitled "Syringe Having a Collapsible Plunger Rod" filed Aug. 21, 2009; and 61/235,848 entitled "Magnifying Collapsed Plunger Rod" filed Aug. 21, 2009, the disclosures of each of which are hereby incorporated by reference in their entirety.

BACKGROUND OF THE INVENTION

1. Field of the Invention

The present invention relates to a hypodermic syringe that has a compact size, and includes a plunger mechanism positioned externally adjacent the syringe when filled.

2. Description of Related Art

Syringe assemblies, and in particular hypodermic syringes, are well known in the medical field for dispensing fluids, such as medication. A conventional syringe typically includes a syringe barrel with an opening at one end and a plunger mechanism disposed through the other end. The plunger typically includes a plunger rod extending through the barrel, with a plunger head or stopper at the end of the plunger rod within the barrel and with a finger flange at the other end of the plunger rod extending out of the barrel. In use, the plunger rod is retracted through the syringe barrel to aspirate or fill the syringe barrel with a fluid, such as a medication, with the plunger rod extending out from the rear end of the syringe barrel. For delivery of the medication to a patient, the opening of the syringe barrel is adapted for fluid communication with a patient, such as through a hypodermic needle fitted at the front end of the syringe barrel or through a luer-type fitting extending from the front end of the syringe barrel for attachment with a fluid line of a patient. Upon depressing of the plunger rod, the plunger rod and stopper travel through the syringe barrel, thereby forcing the contents of the syringe out through the opening at the front end for delivery to the patient. Such an operation is well known in the medical field, and medical practitioners have become well accustomed to the use of such common fluid delivery procedures through standard syringes.

Conventional syringes are well known to be used in connection with a vial of a medication, where the user draws the fluid into the syringe immediately prior to injection and delivery of the fluid to the patient. Oftentimes, hypodermic syringes may be packaged as "pre-filled" devices, wherein the syringe is pre-filled with medication prior to being packaged and delivered to the end user. In this manner, there is no need for the user to fill the device prior to injection, thereby saving time for the end user and maintaining consistent volumes for delivery.

Packaging of such pre-filled syringes, however, tends to be bulky. A pre-filled syringe is typically packaged with the opening at the front end of the barrel including a separate cap thereover and with the plunger rod retracted out of the back end of the syringe barrel, with the fluid pre-filled within the syringe barrel. Such packaging creates an elongated package that can be awkward for shipping and storage.

Pre-filled syringes and pre-filled metered dose syringes are often filled with narcotics or other drugs at a production facility, packaged, and then shipped to a medical facility. Once at the facility, these syringes are often placed in controlled storage and/or locked cabinets to reduce theft of the syringes themselves and/or through of the contents of these syringes. The space within these controlled storage locations is often limited, thus there is a need for a syringe assembly that has a smaller packing footprint, to reduce the storage space required for containing the syringe. It is also desirable to produce syringes that are uniform in terms of an outer surface shape to allow for stacking of these syringes within the storage cabinet.

Typical pre-filled hypodermic syringes have elongated plunger rods extending from beyond the proximal end of a syringe barrel to move the stopper through an injection cycle within the syringe barrel by linear actuation of the elongated plunger rod. This arrangement increases the length of the packaged syringe assembly, which increases costs associated with packaging the pre-filled syringe and takes up additional storage space.

SUMMARY OF THE INVENTION

Accordingly, there is a general need for a hypodermic syringe that has a reduced length and width when the syringe barrel is filled with a liquid medication prior to injection.

According to an embodiment of the present invention, a syringe assembly is provided. The syringe assembly includes: a syringe barrel having an exterior surface, an inside surface defining a chamber, an open proximal end, a distal end, and an outlet disposed adjacent the distal end in fluid communication with the chamber; and a plunger assembly disposed at least partially within the syringe barrel. The plunger assembly includes an elongated plunger rod and a plunger head, the elongated plunger rod being associated with the plunger head to move the plunger head within the chamber of the syringe barrel through an injection cycle. The plunger rod is adapted to move from a collapsed position extending alongside the exterior surface of the syringe barrel to an extended position engaging the plunger head to move the plunger head through the injection cycle.

The plunger rod may be slidably disposed on the syringe barrel. The plunger rod includes a handle portion and at least two flexible legs extending distally from the handle portions. The at least two flexible legs are slidable with respect to the syringe barrel and the plunger head so that the plunger rod is movable from the collapsed position wherein the flexible legs extend alongside and wrap over the exterior surface of the syringe barrel and the extended position wherein the flexible legs engage the plunger head to move the plunger head through the injection cycle. Each of the at least two flexible legs includes a hook formed at a distal end of the flexible leg, the hook being adapted to engage the plunger head. The handle portion is disposed proximate to the proximal end of the syringe barrel in the collapsed position.

The syringe barrel may further include an outwardly extending flange disposed at the open proximal end of the syringe barrel, the outwardly extending flange having at least two apertures defined therein. The at least two flexible legs of the plunger rod extend through the at least two apertures in the outwardly extending flange in the collapsed position.

The syringe barrel may, alternatively, further include at least two slots extending between the inside surface and the exterior surface of the syringe barrel. The at least two flexible legs of the plunger rod extend through the at least two slots in the syringe barrel in the collapsed position.

The plunger head includes a stopper having a proximal surface, a distal surface, and a peripheral surface extending between the proximal surface and the distal surface, the peripheral surface including at least one sealing surface for sealingly engaging the inside surface of the syringe barrel. The plunger head further includes a stopper adapter disposed on the distal surface of the stopper, the stopper adapter being adapted to engage the plunger rod during the injection cycle. The stopper adapter is at least partially hollow and includes a sidewall having at least two slots defined therein. The plunger rod includes a handle portion and at least two flexible legs extending distally from the handle portions, the at least two flexible legs being slidable with respect to the syringe barrel and the plunger head so that the plunger rod is movable from a collapsed position wherein the flexible legs extend through the at least two slots in the sidewall of the stopper adapter alongside and adjacent to the exterior surface of the syringe barrel and an extended position wherein distal ends of the flexible legs engage the slots in the stopper adapter to move the plunger head through the injection cycle.

The exterior surface of the syringe barrel may include a recessed grip portion defined therein. The recessed grip portion may include an over-molded gripping surface and/or a plurality of gripping dimples.

According to an alternative embodiment of the present invention, the plunger rod extends substantially parallel with the exterior surface of the syringe barrel in the collapsed position and extends substantially in line with a longitudinal axis of the syringe barrel in the extended position. The plunger rod includes a first end and a second end, and an attachment member located at the second end. The attachment member on the plunger rod secures the plunger rod to the plunger head in the extended position. The plunger head includes a stopper having a proximal surface, a distal surface, and a peripheral surface extending between the proximal surface and the distal surface, the peripheral surface including at least one sealing surface for sealingly engaging the inside surface of the syringe barrel. The plunger head further includes a stopper adapter disposed on the distal surface of the stopper, the stopper adapter being adapted to engage the plunger rod during the injection cycle.

The syringe assembly according to the alternative embodiment further includes a flange located at the proximal end of the syringe barrel, the flange including an opening in alignment with an opening in the stopper adapter through which the plunger rod extends. Movement of the plunger rod from the collapsed position to the extended position includes pivoting the second end of the plunger rod in a radial direction with respect to the syringe barrel and then applying a proximal force to the plunger rod to axially slide the plunger rod through the openings in the flange and the stopper adapter and secure the attachment member on the second end of the plunger rod with the stopper adapter. The plunger rod includes a thumb press member located at said first end of said plunger rod and is located above the proximal end of the syringe barrel.

According to still another embodiment of the present invention, a method of actuating a syringe assembly is provided. The method includes the step of providing a syringe assembly that includes a syringe barrel having an exterior surface, an inside surface defining a chamber, an open proximal end, a distal end, and an outlet disposed adjacent the distal end in fluid communication with the chamber; and a plunger assembly disposed at least partially within the syringe barrel, the plunger assembly including an elongated plunger rod and a plunger head, the plunger rod including a handle portion and at least two flexible legs extending distally from the handle portion and the plunger head including a stopper and a stopper adapter disposed on a distal surface of the stopper. Each of the at least two flexible legs includes a hook formed at a distal end of the flexible leg. The syringe barrel further includes at least two openings defined therein. The plunger rod is disposed in a collapsed position relative to the syringe barrel and the plunger head with the at least two flexible legs extending through the at least two openings in the syringe barrel and alongside and adjacent to the exterior surface of the syringe barrel and the handle portion positioned proximate to the proximal end of the syringe barrel. The plunger rod is then withdrawn from the collapsed position such that the hooks of the at least two flexible legs pass through the at least two openings in the syringe barrel. The stopper adapter is then engaged with the hooks of the at least two flexible legs to lock the plunger rod into engagement with the plunger head. The plunger assembly is then advanced within the chamber of the syringe barrel so that the stopper slides within the chamber with respect to the syringe barrel in a distal direction. The syringe barrel further includes an outwardly extending flange disposed at the open proximal end of the syringe barrel and the at least two openings are apertures defined in the outwardly extending flange or, alternatively, at least two openings are slots extending between the inside surface and the exterior surface of the syringe barrel.

Further details and advantages of the invention will become clear upon reading the following detailed description in conjunction with the accompanying drawing figures, wherein like parts are designated with like reference numerals throughout.

BRIEF DESCRIPTION OF THE DRAWINGS

FIGS. 5A-5F are perspective views of the syringe assembly according to the present invention shown in successive views during an activation and injection cycle, with FIG. 5A showing the plunger mechanism in a first state prior to activation; FIG. 5B showing the plunger mechanism during initial retraction; FIG. 5C showing the plunger mechanism in a fully retracted state; FIG. 5D showing the plunger mechanism just prior to the injection cycle; FIG. 5E showing the plunger mechanism during the injection cycle; and FIG. 5F showing the plunger mechanism after completion of the injection cycle with the plunger head bottomed out.

DESCRIPTION OF PREFERRED EMBODIMENTS

For purposes of the description hereinafter, spatial orientation terms, if used, shall relate to the referenced embodiment as it is oriented in the accompanying drawing figures or otherwise described in the following detailed description. However, it is to be understood that the embodiments described hereinafter may assume many alternative variations and embodiments. It is also to be understood that the specific devices illustrated in the accompanying drawing figures and described herein are simply exemplary and should not be considered as limiting.

Figure 1:
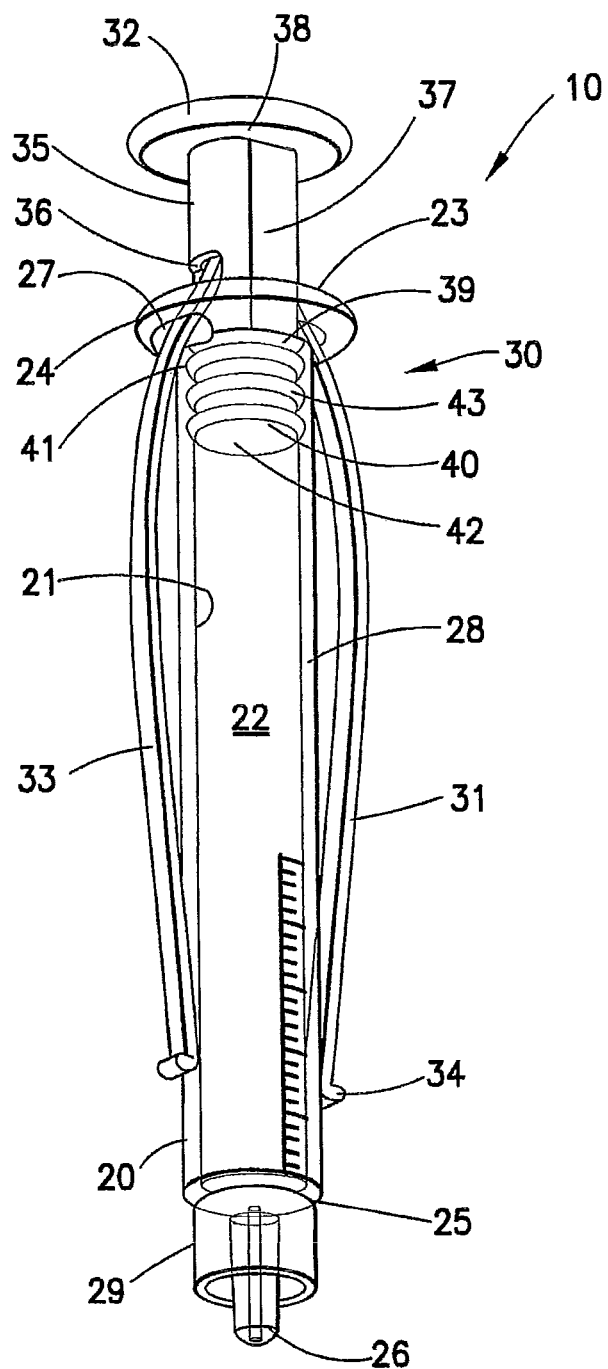
FIG. 1 is a perspective view of a syringe assembly according to an embodiment of the present invention.

Referring to FIG. 1, a syringe assembly 10 according to an embodiment of the present invention is shown. The syringe assembly 10 includes a syringe barrel 20 and a plunger assembly 30. As shown in FIG. 1, the syringe barrel 20 has an open proximal end 23 and a distal end 25 opposite to the open proximal end 23. The syringe barrel 20 has an inside surface 21, which defines a chamber 22. As shown, the syringe barrel 20 may have a cylindrical or substantially cylindrical shape, though it is to be appreciated that the syringe barrel 20 may be formed in any suitable shape. Additionally, the syringe barrel 20 may be formed of glass, or may be injection molded from thermoplastic material such as polypropylene and polyethylene according to techniques known to those of ordinary skill in the art, though it is to be appreciated that the syringe barrel 20 may be made from other suitable materials and according to other applicable techniques.

The syringe barrel 20 also includes a substantially conical outlet tip 26 disposed on the distal end 25 of the syringe barrel 20 in the form of a conventional luer fitting. The outlet tip 26 is in fluid communication with the chamber 22 of the syringe barrel 20. A needle cannula (not shown) may be attached to the outlet tip 26 such that an interior of the needle cannula is in fluid communication with the chamber 22 of the syringe barrel 20. The needle cannula may be secured within the outlet tip 26 by a chemical adhesive, such as epoxy, or may be mechanically affixed to the outlet tip 26 according to known techniques. Alternatively, syringe assembly 10 is contemplated for use in connection with a separate needle assembly (not shown) such as through a standard luer slip fitting or luer lock fitting type connection with syringe assembly 10 at the outlet tip 26, or alternatively to a separate intravenous (IV) connection assembly (not shown). As such, a threaded luer collar 29 may further be provided for threaded engagement with such a separate mechanism, as is known in the art.

The syringe assembly 10 may also include a protective cap (not shown) disposed over the outlet tip 26 to protect the needle cannula prior to use and to prevent accidental needle sticks of persons handling the syringe assembly 10 prior to use. An annular ridge (not shown) may be formed on the distal end 25 of the syringe barrel 20 to facilitate attachment of a protective cap or a standard needle hub over the outlet tip 26. An outwardly extending flange 24 may also be provided at the proximal end 23 of the syringe barrel 20 to assist in handling of the syringe assembly 10. The outwardly extending flange 24 may have a pair of opposing apertures 27 extending through the flange 24.

With further reference to FIG. 1, the syringe assembly 10 also includes a plunger assembly 30 disposed at least partially within the syringe barrel 20. The plunger assembly 30 includes a flexible, elongated plunger rod 31 that is slidably disposed on the syringe barrel 20. The plunger rod 31 includes a handle portion 32 at the proximal end of the plunger rod 31 and a pair of flexible legs 33 extending distally from the handle portion 32. The flexible legs 33 each have a hook 34 formed at their distal ends. The plunger assembly 30 also includes a plunger head in the form of stopper 40 disposed within the chamber 22 of the syringe barrel 20. The stopper 40 includes a proximal surface 41, a distal surface 42, and a peripheral surface 43 extending between the proximal 41 and distal 42 surfaces. The peripheral surface 43 of the stopper 40 includes one or more sealing surfaces such as an annular rib so that the stopper 40 sealingly engages the inside surface 21 of the syringe barrel 20 so as to seal the chamber 22.

A stopper adapter 35 is formed as an at least partially hollow cylindrical member having a sidewall 37 extending between a proximal end 38 and a distal end 39. The distal end 39 of the stopper adapter 35 is attached to the proximal surface 41 of the stopper 40. A pair of slots 36 is formed in the sidewall 37 of the stopper adapter 35 so that the flexible legs 33 of the plunger rod 31 may pass through the stopper adapter 35 from the proximal end 38 of the stopper adapter 35 and through the sidewall 37 via the slots 36 during use in an injection cycle, as will be described in further detail herein.

In the initial position illustrated in FIG. 1, the plunger rod 31 is in a collapsed position with the flexible legs 33 extending through the slots 36 in the sidewall 37 of the stopper adapter 35 as well as the apertures 27 in the outwardly extending flange 24 and alongside and adjacent to the exterior surface 28 of the syringe barrel 20 to wrap over or around the exterior surface 28 of the syringe barrel 20 with the handle portion 32 of the plunger rod 31 positioned proximate to the proximal end 23 of the syringe barrel 20, which minimizes the overall length of the syringe assembly 10.

It is to be appreciated that the syringe assembly 10 according to the present embodiment is particularly suitable for use as a pre-filled syringe with the stopper 40 provided at the proximal end 23 of the syringe barrel 20. Alternatively, the plunger rod 31 could be used to pull the stopper 40 proximally so as to aspirate an empty syringe barrel 20. Syringe assembly 10 may be further provided with a mechanism so as to prevent re-use of the device. For example, the engagement between plunger rod 31 and stopper 40 as provided through flexible legs 33 and stopper adapter 35 may be a one-way engagement, in that flexible legs 33 lock into stopper adapter 35 prior to the injection cycle, but once the injection cycle is complete, any attempt to retract the plunger rod in the opposite direction will cause the attachment between flexible legs 33 and stopper adapter 35 to detach or otherwise break or shear, thereby preventing re-use of the device.

It is also to be appreciated that the syringe assembly 10 according to the present embodiment allows for the overall length and width of a pre-filled syringe to be minimized for packaging and storage savings and to reduce storage space in medicine drawers. For instance, the syringe assembly 10 according to the present embodiment achieves approximately 70% reduction in length in the packaged pre-filled syringe.

Figure 2:
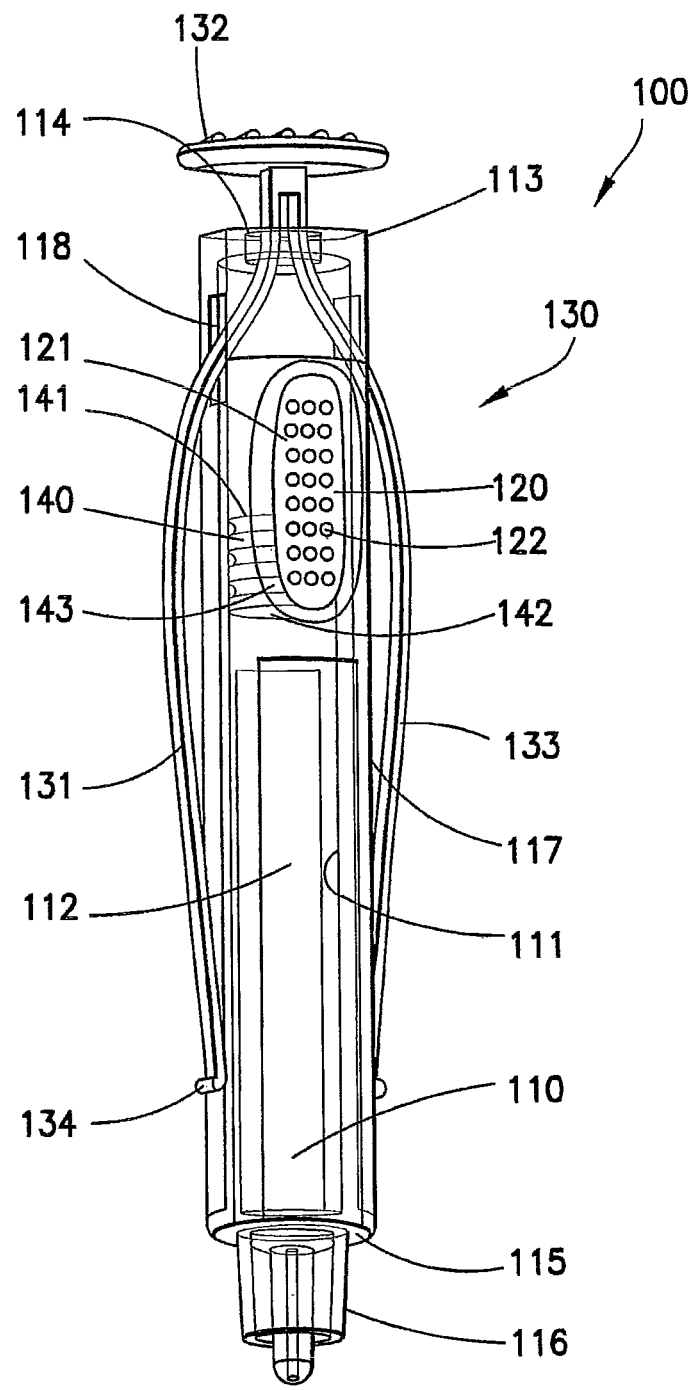
FIG. 2 is a perspective view of a syringe assembly according to a further embodiment of the present invention.
Figure 3:
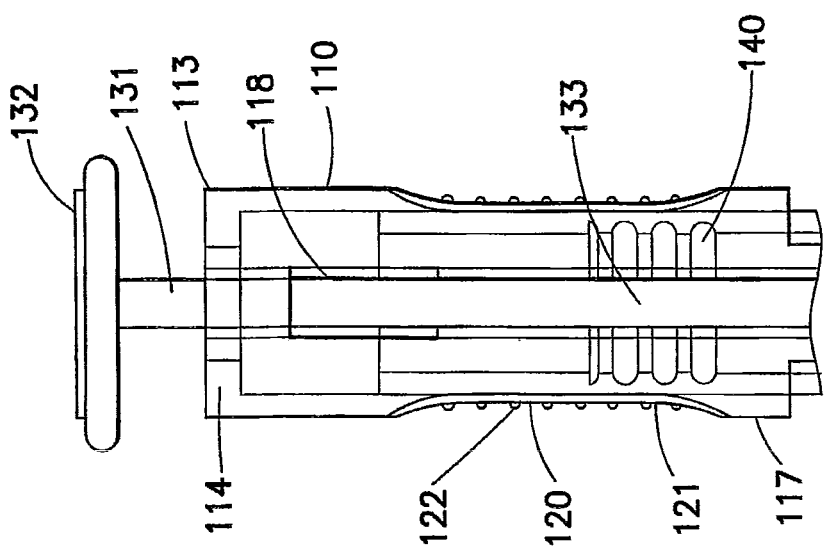
FIG. 3 is a partial side view of the syringe assembly shown in FIG. 2.

With reference to FIGS. 2 and 3, a syringe assembly 100 according to a further embodiment of the present invention is shown. The syringe assembly 100 operates in a manner similar to the syringe assembly 10 discussed above with reference to FIG. 1 and as will be further detailed below with reference to FIGS. 5A-5F. The syringe assembly 100 includes a syringe barrel 110 and a plunger assembly 130. As shown in FIG. 2, the syringe barrel 110 has an open proximal end 113 and a distal end 115 opposite to the open proximal end 113. The syringe barrel 110 has an exterior surface 117 extending between the proximal 113 and distal 115 ends and an inside surface 111, which defines a chamber 112. The syringe barrel 110 also includes an outlet 116 disposed on the distal end 115 of the syringe barrel 110. The outlet 116 is in fluid communication with the chamber 112 of the syringe barrel 110.

As shown in FIGS. 2 and 3, the exterior surface 117 of the syringe barrel 110 is formed with a recessed grip region 120 that assists in holding the syringe assembly 100. Typical outwardly extending syringe flanges used to provide a gripping area for a syringe assembly are obtrusive and cause inefficiencies in storage due to their wide shape. By recessing a grip region 120 into the syringe barrel 110, there will be no need for an outwardly extending flange. An exterior surface 121 of the recessed grip region 120 may be over-molded to provide a better gripping surface or may include gripping dimples 122.

With further reference to FIGS. 2 and 3, a plunger assembly 130 includes a flexible, elongated plunger rod 131. The plunger rod 131 includes a handle portion 132 at the proximal end of the plunger rod 131 and one or more of flexible legs 133 extending distally from the handle portion 132. While the embodiment is shown with a pair of flexible legs 133, it is contemplated that any number of flexible legs 133 can be provided. For example, in certain embodiments, the use of three flexible legs may provide an appropriate balanced bending moment of inertia for any axis of bending. The flexible legs 133 each have a hook 134 formed at their distal ends. The plunger assembly 130 also includes a stopper 140 disposed within the chamber of the inner syringe barrel 110. The stopper 140 includes a proximal surface 141, a distal surface 142, and a peripheral surface 143 extending between the proximal 141 and distal 142 surfaces. The peripheral surface 143 of the stopper 140 includes one or more sealing surfaces so that the stopper 140 sealingly engages the inside surface 111 of the syringe barrel 110 to seal the chamber 112 of the syringe barrel 110.

The flexible legs 133 extend through slots 118 in the syringe barrel 110 proximate to the proximal end 113 of the syringe barrel 110 and alongside and adjacent to the exterior surface 117 of the syringe barrel 110 to wrap over or around the exterior surface 117 of the syringe barrel 110 with the handle portion 132 of the plunger rod 131 positioned proximate to the proximal end 113 of the syringe barrel 110, which minimizes the overall length of the syringe assembly 100. When it is time to use the syringe assembly 100, a user can pull the plunger rod 131 proximally to an extended position. An inwardly extending proximal stop 114 is provided at the proximal end 113 of the syringe barrel 110 to engage the hooks 134 at the ends of the flexible legs 133 and prevent removal of the plunger rod 131 from the syringe barrel 110.

Once the flexible legs 133 are withdrawn from the exterior surface 117 of the syringe barrel 110, the plunger rod 131 is pushed forward so that the legs 133 mate with the proximal surface 141 of the stopper 140 to connect the plunger rod 131 with the stopper 140 such that the plunger rod 131 can actuate the stopper 140 through an injection cycle. To that end, the stopper 140 may be provided with a stopper adapter 135 extending from the proximal surface 141 of the stopper 140 to facilitate the engagement between the plunger rod 131 and the stopper 140 as is more clearly shown in FIGS. 5A-5F. The stopper adapter 135 is similar to the stopper adapter 35 discussed above with reference to FIG. 1.

Figure 5A:
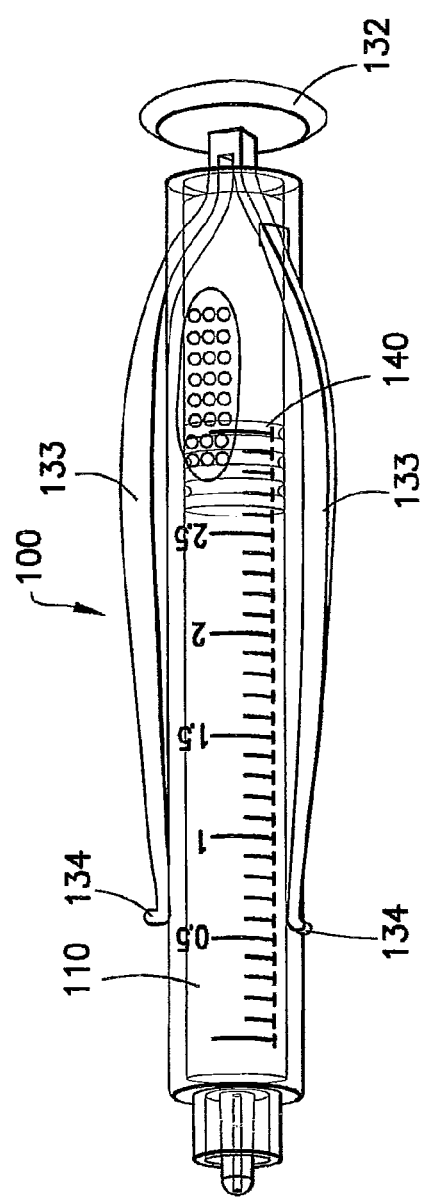

Use of the device according to the embodiment of FIGS. 2 and 3 will be described in connection with FIGS. 5A-5F, with continuing reference to the features of FIGS. 2 and 3. Initially, the plunger rod 131 is in a collapsed position, as shown in FIG. 5A, with the flexible legs 133 extending through the stopper adapter 135 and the slots 118 in the syringe barrel 110 and alongside and adjacent to the exterior surface 117 of the syringe barrel 110 to wrap over or around the exterior surface 117 of the syringe barrel 110 with the handle portion 132 of the plunger rod 131 positioned proximate to the proximal end 113 of the syringe barrel 110, which minimizes the overall length of the syringe assembly 100.

Figure 5B:
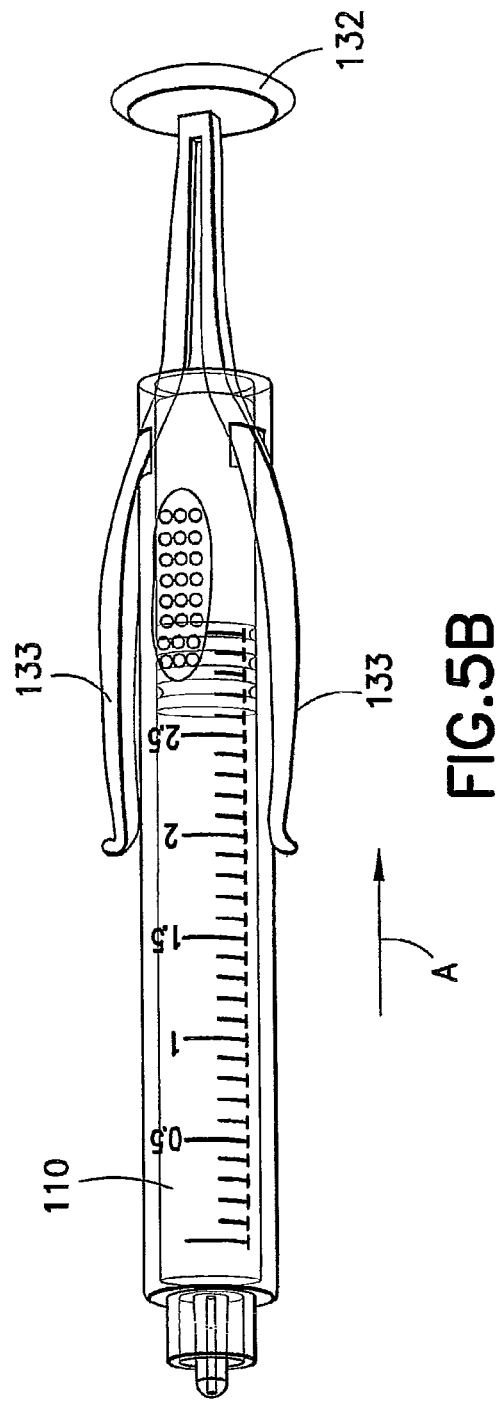

When it is time to use the syringe assembly 100, a user can pull the plunger rod 131 proximally in the direction of arrow A as shown in FIG. 5B, toward proximal end 113. During such movement, flexible legs 133 travel through slots 118 near the proximal end 113 of syringe barrel 100, to an extended position as shown in FIG. 5C in which the plunger rod 131 is in a fully retracted state. At this point with plunger rod 131 in an extended position, flexible legs 133 are adapted to be locked into engagement with the stopper adapter 135. This may be accomplished with flexible legs 133 flexing inward as shown at arrows B in FIG. 5C. Such engagement may be automatic, with flexible legs 133 biased in a direction of arrows B, or alternatively, may require a user to press radially against flexible legs 133 in the direction of arrows B.

Figure 5E:
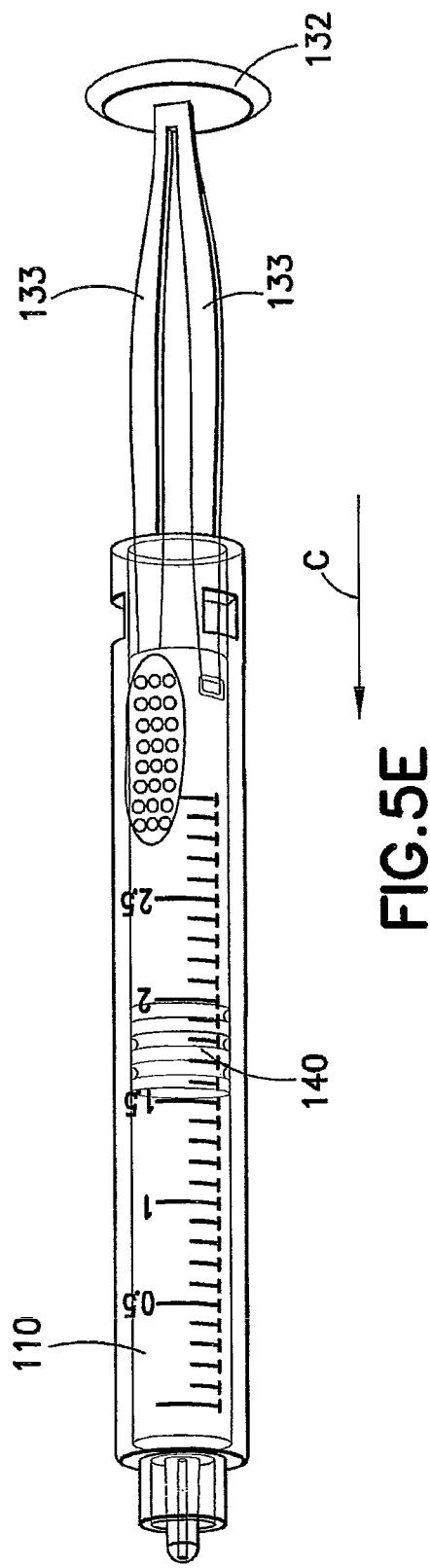
Figure 5F:
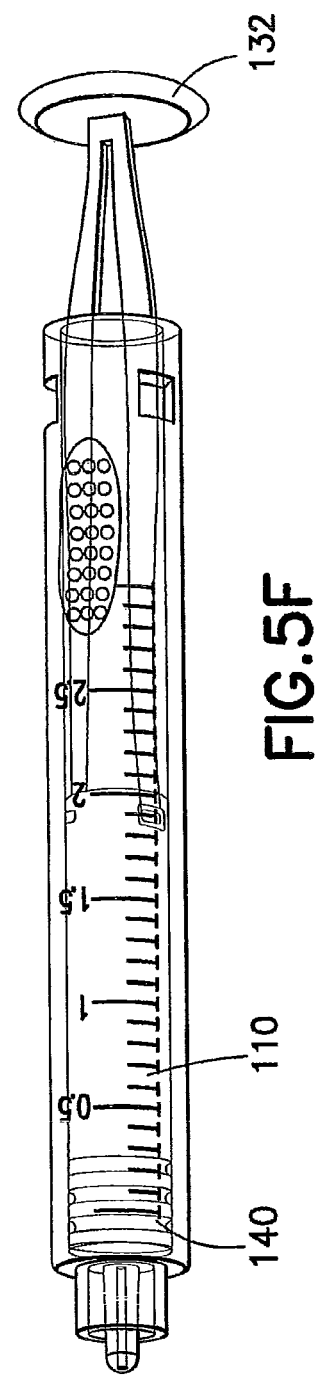

In any event, such flexing of flexible legs 133 causes the hooks 134 at the ends of the flexible legs 133 to lock into engagement with the stopper adapter 135, as shown in FIG. 5D, such that the stopper adapter 135 and the stopper 140 may be pushed (and pulled) via the plunger rod 131. With the plunger rod 131 in an extended position engaging the stopper 140 via the stopper adapter 135, the user may then push distally on the plunger rod 131 in a direction of arrow C in FIG. 5E, thereby causing stopper 140 to move linearly axially within the chamber 112 of the syringe barrel 110 through an injection cycle to inject the contents of the syringe barrel 110, as shown in FIG. 5E. At the end of the injection cycle, stopper 140 is bottomed out within syringe barrel 110. Syringe assembly 100 can thereafter be properly discarded in an appropriate sharps disposal container.

Figure 4:
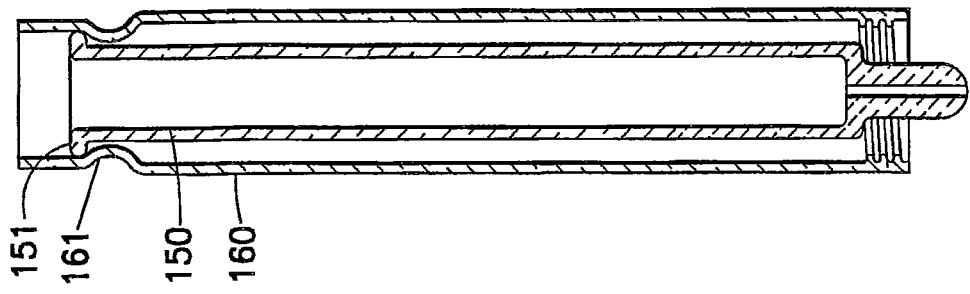
FIG. 4 is partial cross-sectional view of a syringe barrel and outer tube of a syringe assembly according to yet another embodiment of the present invention.

With reference to FIG. 4, another embodiment of a syringe assembly according to the present invention is shown. The syringe assembly includes an inner glass syringe barrel 150 having an outwardly extending flange 151 at a proximal end thereof. In order to provide for a glass syringe assembly having a more compact width, an outer plastic tube 160 having a recessed, inverted flange 161 is disposed over the syringe barrel 150 such that the interior surface of the inverted flange 161 engages the outwardly extending flange 151 of the syringe barrel 150 to retain the outer plastic tube 160 on the syringe barrel 150. The exterior surface of the inverted flange 161 acts to provide a gripping area for the syringe assembly in a similar manner to the recessed grip area 120 of the syringe barrel 110 illustrated in FIG. 2.

It is further contemplated that syringe assembly 10, 100 may be provided as an integrated product without the need for any external packaging to maintain sterility. In such an embodiment, it is contemplated that a tip cap (not shown) can be provided at the distal end of syringe barrel 20, 110, such as a cap fully surrounding and encompassing the outlet tip 26, and any luer collar or other fitting extending about the distal end 25, 115. Such a tip cap provides for sterility of the contents of syringe barrel 20, 110 as well as the tip thereof. Moreover, proximal end 23, 113 of syringe barrel 20, 110 may also be sealed to provide for sterility, such as through a removable or breakable membrane.

In one embodiment, it is contemplated that handle 32, 132 at the proximal end of plunger rod 31, 131 may be in sealing contact with the proximal end 23, 113 of syringe barrel 20, 110, such as at flange 24. Such sealing contact may be a breakable contact, which maintains sterility until a seal is actively broken by a user. In this manner, with a tip cap on the front end and such a seal at the rear end, syringe assembly 10, 100 can be provided as a fully packaged product requiring no additional outer packaging.

Figure 6:
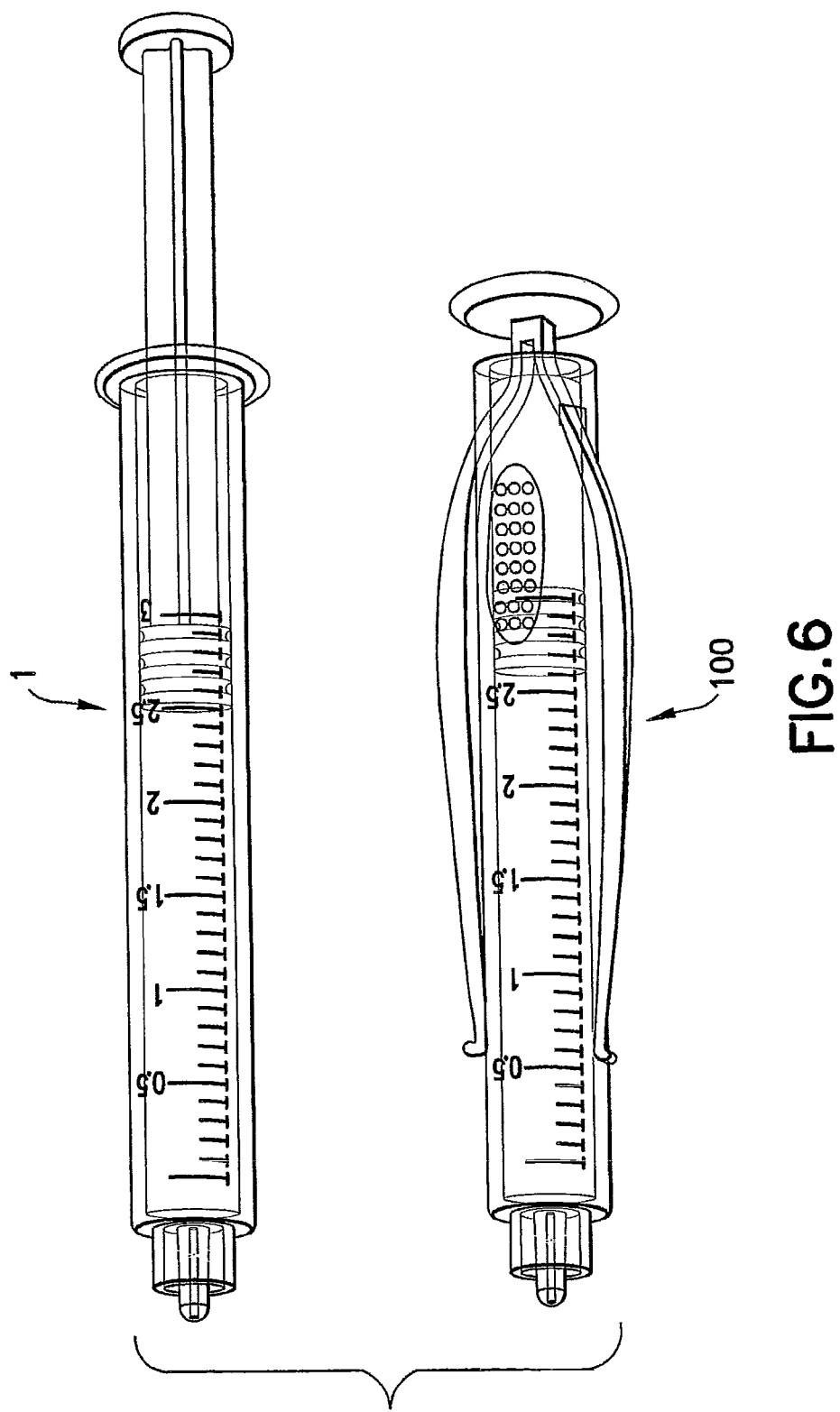
FIG. 6 is a perspective view comparing a conventional syringe to a syringe assembly in accordance with the present invention.

With such an arrangement, the overall size and shape of syringe assembly 10, 100 when filled for use is of an overall profile similar to a conventional syringe after use with a plunger completely extended within a syringe barrel, as seen in FIG. 6, which depicts the profile of a conventional syringe 1 in comparison to syringe assembly 100 in accordance with the present invention. As such, the profile is significantly reduced from that of a conventional pre-filled syringe, which includes the plunger retracted from the barrel prior to use.

Figure 7:
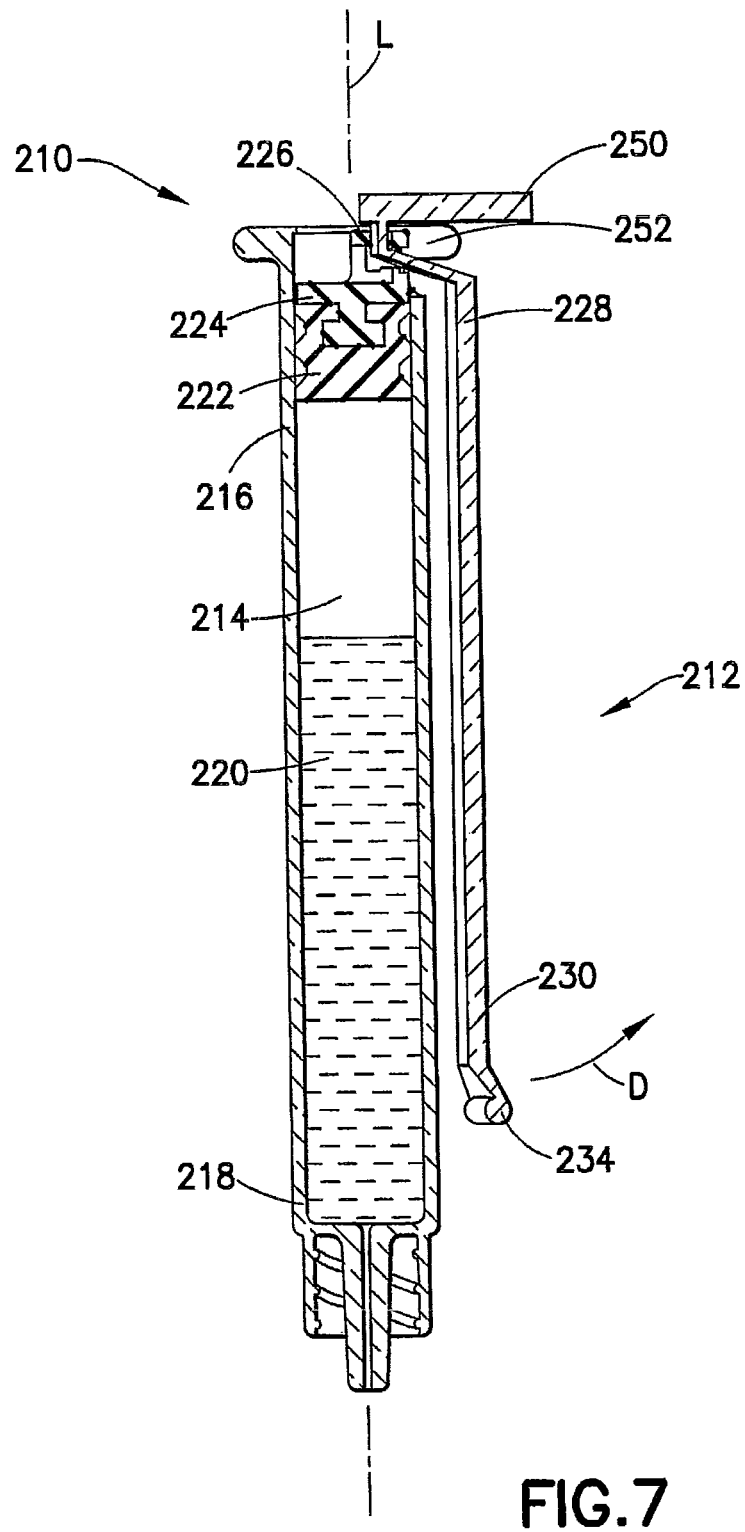
FIG. 7 is a side elevation view of a syringe assembly according to another embodiment of the present invention, including the collapsed plunger rod of the present invention in a pre-use position.

Reference is now made to FIGS. 7-9C, which show a syringe assembly according to a further embodiment of the present invention, generally indicated as 210, having a collapsed plunger rod, generally indicated as 212, according to the present invention. The syringe barrel 214 has a proximal end 216, a distal end 218, and a sidewall 220 extending between the proximal end 216 and the distal end 218. A stopper 222 is located within the syringe barrel 214 and a stopper adapter 224 is associated with the stopper 222. The stopper adapter 224 may be integrally formed with the stopper 222 or may be a separately molded member having a first end secured to the stopper 222. The syringe barrel 214, stopper 222, and stopper adapter 224 define a longitudinal axis L, as shown in FIG. 7. The plunger rod 212 may be secured to the stopper adapter 224 and is configured for cooperation with the stopper adapter 224 to move from a collapsed pre-use position to an expanded ready-to-use position.

In one embodiment, the plunger rod 212 is adapted to transition from the pre-use position in which the plunger rod 212 extends substantially parallel with and alongside and adjacent to the sidewall 220 of the syringe barrel 214, to the expanded ready-to-use position in which the plunger rod 212 extends substantially in line with the longitudinal axis of the syringe barrel 214, stopper 222, and the stopper adapter 224. In one embodiment, the plunger rod 212 includes a first end 228 and a second end 230 with an attachment member 232 disposed adjacent the second end 230. The stopper adapter 224 may include a joining end 226 configured for connection with the attachment member 232 of the plunger rod 212 in the ready-to-use position.

According to one design, a containing member 236 may be provided adjacent a cut-out portion 246 or recessed groove in the proximal end 216 of the syringe barrel sidewall 220, which is dimensioned to allow a portion of the plunger rod 212 to pass therethrough. The cut-out portion 246 may also be dimensioned such that the first end 228 and the second end 230 may not pass through the cut-out portion 246 and are restrained by the containing member 236 preventing inadvertent separation of the plunger rod 212 from the syringe assembly 210 in the initial pre-use position or during transition of the plunger rod 212 to the ready-to-use position.

Outward or pivotal movement by a clinician in the direction of arrow shown in FIG. 7 can dislodge the plunger rod 212 from the syringe barrel sidewall 220 and dislodge the plunger rod 212 from the joining end 226 of the stopper adapter 224 for activation of the plunger rod 212 to the expanded ready-to-use state. During transition of the syringe assembly 210 from the initial position to the ready-to-use position, the plunger rod 212 is advanced in an angled substantially proximal direction as shown by arrow E of FIG. 8A.

Figure 8A:
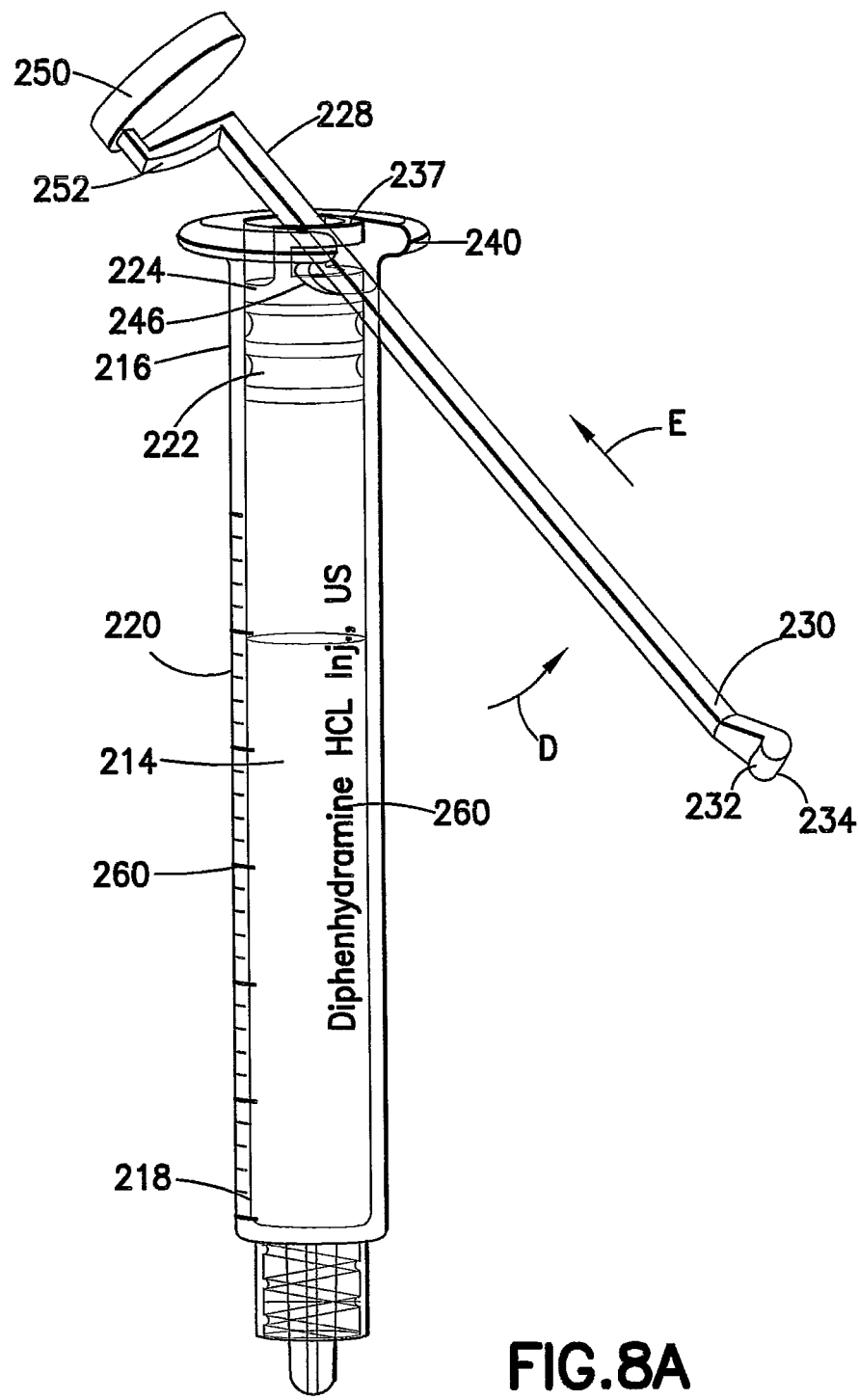
FIG. 8A is a perspective view of the syringe assembly of FIG. 7, having a plunger rod pivoted away from the syringe barrel during transition of the syringe from the initial position to the ready-to-use position.
Figure 8B:
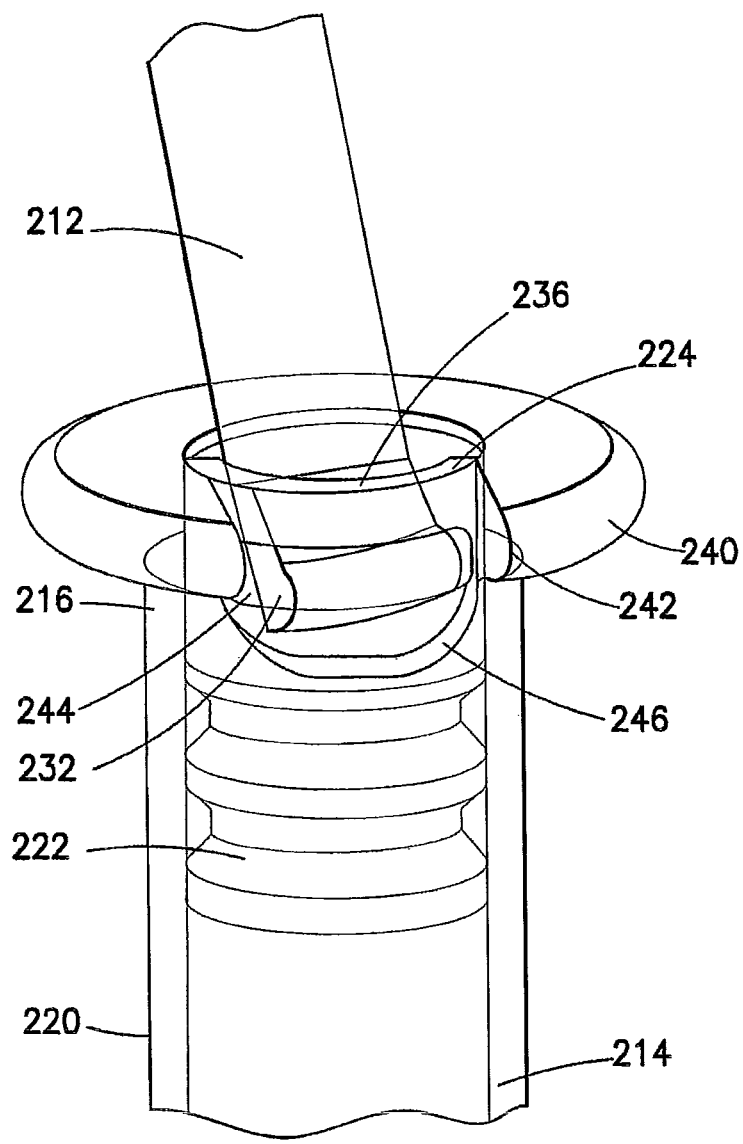
FIG. 8B is a partial perspective view of the syringe assembly of FIG. 8A showing engagement of the plunger rod during transition of the syringe from the initial position to the ready-to-use position.
Figure 8C:
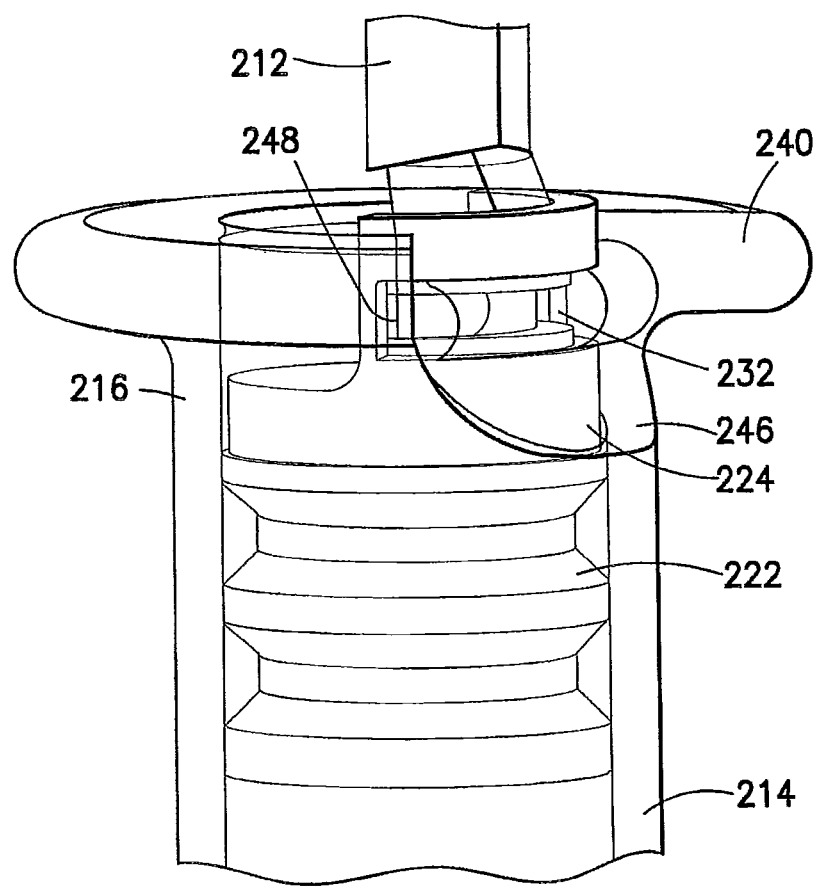
FIG. 8C is a partial perspective view of the syringe assembly of FIG. 8A showing engagement of the plunger rod during further transition of the syringe from the initial position to the ready-to-use position.

Reference is now made to FIGS. 8A-8C which shows sequential perspective views of the movement of the collapsed plunger rod 212 into the ready-to-use position. In operation, the plunger rod 212 moves from the collapsed position to the expanded position through a pivoting motion of the second end 230 of the plunger rod 212, as shown in FIG. 8A, in a radial direction with respect to the syringe barrel 214. A subsequent application of a force to the plunger rod 212 in the proximal direction, as shown by arrow E of FIG. 8A causes the plunger rod 212 to slide in an axial direction toward the proximal end 216 of the syringe barrel 214.

The syringe assembly 210 can further include a flange 240 located at the proximal end 216 of the syringe barrel 214. This flange 240 can include an opening 242 which is in alignment with an opening 244 in the stopper adapter 224 through which the plunger rod 212 extends. The cut-out portion 246 can be provided in the proximal end 216 of the syringe barrel sidewall 220 to facilitate movement of the attachment member 232 through the flange opening 242 and the stopper adapter opening 244. Openings 242, 244 and cut-out portion 246 are best shown in FIG. 8B.

Figure 8D:
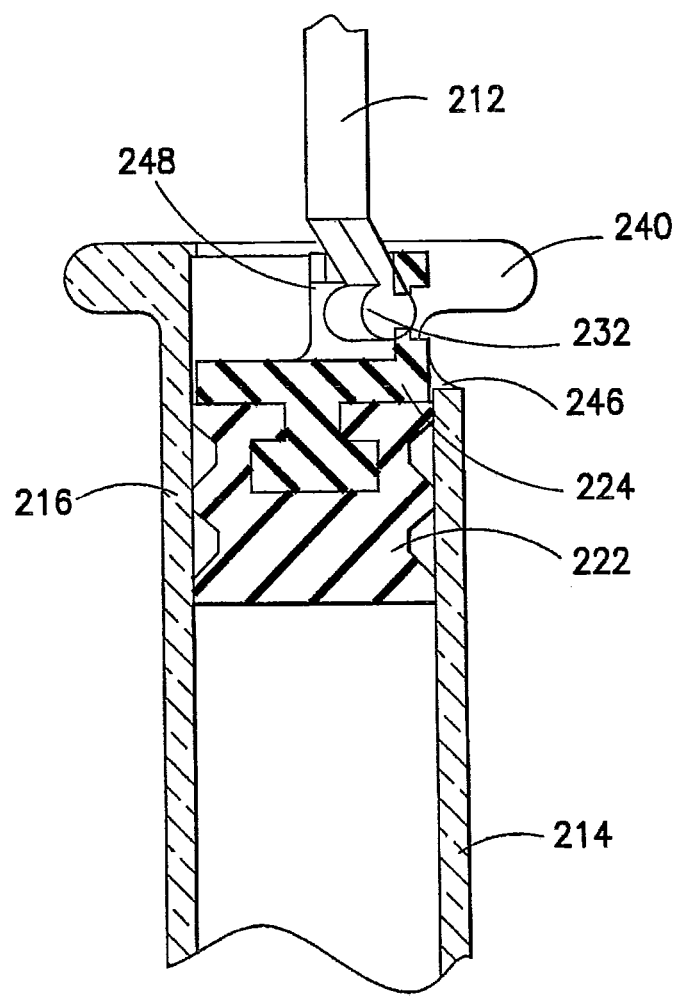
FIG. 8D is a partial front cross-sectional view of the syringe assembly of FIG. 8A in the ready-to-use position.

The applied axial movement causes the plunger rod 212 to move through the openings in the flange 242 and the stopper adapter 244 to align the plunger rod 212 along the longitudinal axis of the syringe barrel 214, stopper 222, and stopper adapter 224. The attachment member 232 on the plunger rod 212 then snaps into the joining end 226 of the stopper adapter 224 to secure the plunger rod 212 thereto in the expanded ready-to-use position. The attachment member 232 can include at least one detent bump 234, shown in FIG. 7, which flexes the plunger rod 212 outward when pulled. The attachment member 232 joined with a receiving member 248 located in the stopper adapter 224 is clearly shown in FIGS. 8B and 8D. FIG. 8D is a partial front cross-sectional view of the syringe assembly 210 having the plunger rod 212 in the ready-to-use position. For purposes of clarity, the plunger rod 212 is not illustrated in cross-section.

Optionally, the plunger rod 212 can include a thumb press member 250 located at the first end 228 thereof. Preferably, this thumb press member 250 is located above the proximal end 216 of the syringe barrel 214 and the flange 240. The plunger rod 212 can include an inwardly curved portion 252 to facilitate manipulation of the plunger rod 212 through the openings 242, 244 and the cut-out portion 246 of the syringe barrel 214.

Figure 9A:
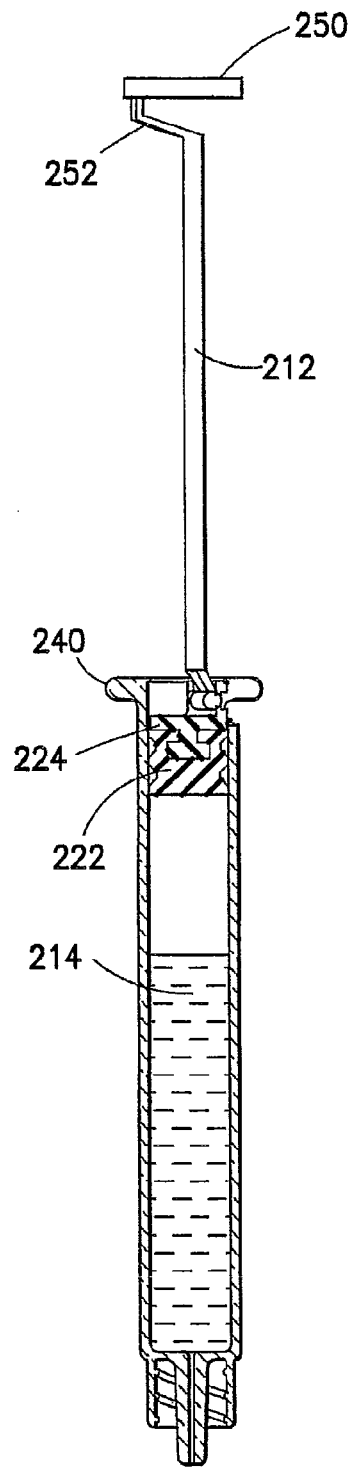
FIG. 9A is a front cross-sectional view of the syringe assembly of FIG. 8A in the ready-to-use position.
Figure 9B:
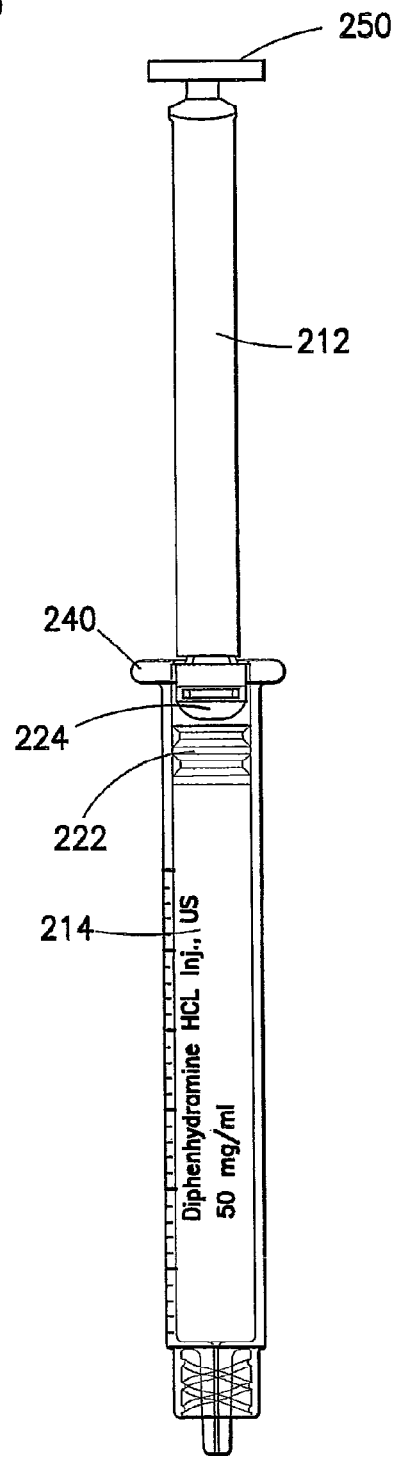
FIG. 9B is a side view of the syringe assembly of FIG. 8A.
Figure 9C:
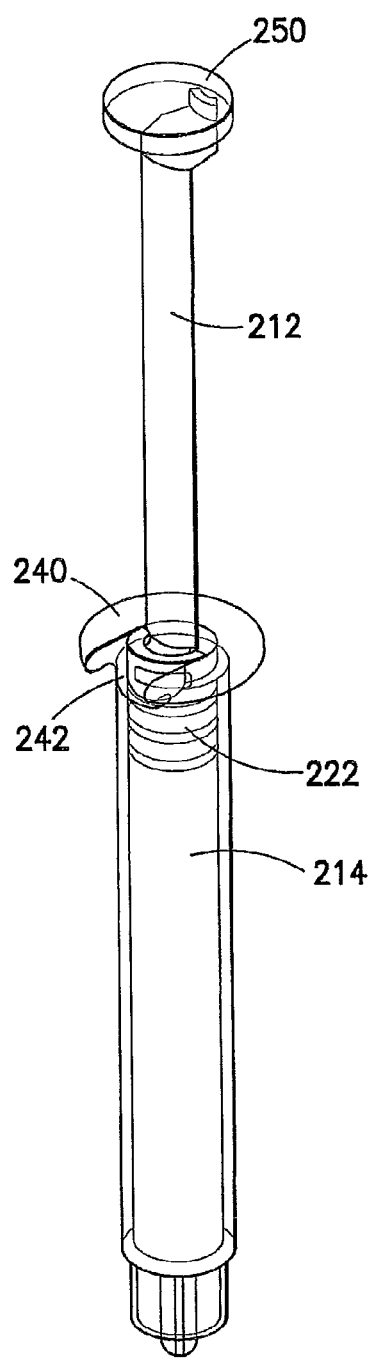
FIG. 9C is a perspective view of the syringe assembly of FIG. 8A.

The application of force to plunger rod 212 can be applied by a pushing motion to the plunger rod 212 or to the second end 230 of the plunger rod 212 and/or by applying a pulling motion to the thumb press member 250. The transition from the partially expanded position of FIG. 8B to the fully expanded position of FIGS. 8C-8D requires the plunger rod 212 to be slightly moved in a radial direction with respect to the stopper adapter 224 and stopper 222 to snap the attachment member 232 into the receiving member 248 of the stopper adapter 224 so that the plunger rod 212 is axially aligned with the longitudinal axis of the syringe barrel 214, stopper adapter 224, and stopper 222, placing the syringe assembly 210 in the ready-to-use position. The syringe assembly 210 is shown in FIGS. 9A-9C in the ready-to-use position having the plunger rod 212 fully extended and engaged with the stopper adapter 224. FIG. 9A is a front cross-sectional view of the syringe assembly 210 having the plunger rod 212 in the ready-to-use position. For purposes of clarity, the plunger rod 212 is not illustrated in cross-section.

Referring to FIGS. 10A-10E, the usage of a syringe assembly 310 having a collapsible plunger rod 312, according to another embodiment of the present invention similar to the embodiment discussed above with reference to FIGS. 7-9C, is demonstrated. As shown, the plunger rod 312 may further include a magnification member 362. The syringe assembly 310 is shown in its initial unused position in FIG. 10A. The plunger rod 312 may have a magnification member 362 disposed over indicia disposed on or with the syringe barrel sidewall 320, allowing a medical practitioner to easily identify the contents and dosing of the syringe assembly 310 prior to use.

Figure 10A:
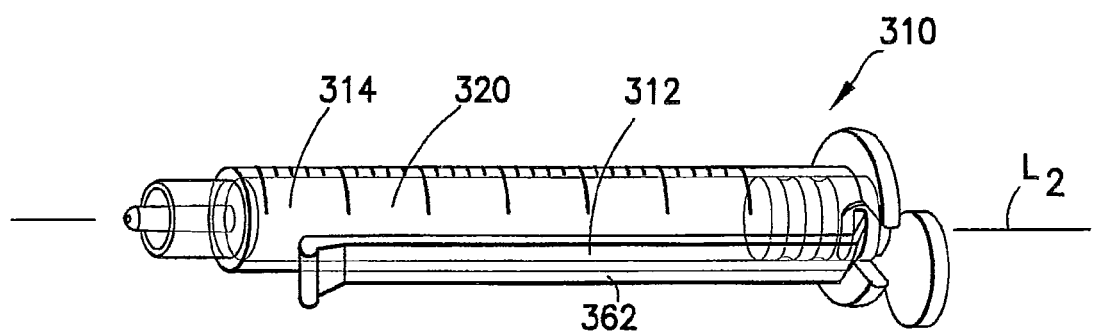
FIG. 10A is a perspective view of the syringe assembly according to another embodiment of the present invention, having a plunger rod in an initial position.
Figure 10B:
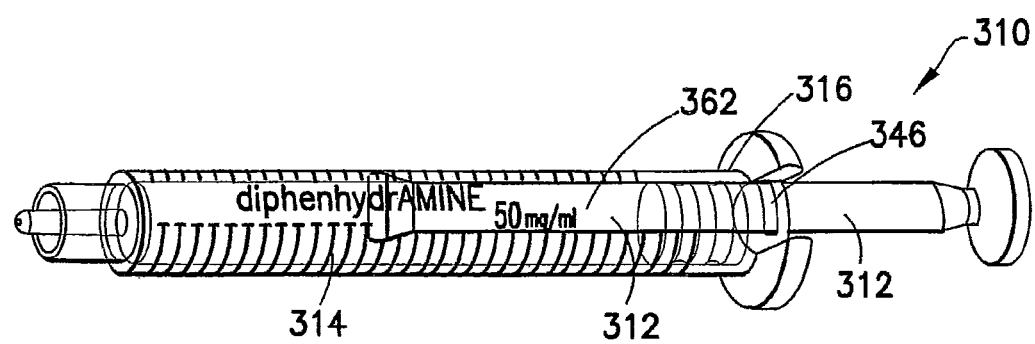
FIG. 10B is a perspective view of the syringe assembly of FIG. 10A having the plunger rod partially axially advanced.
Figure 10C:
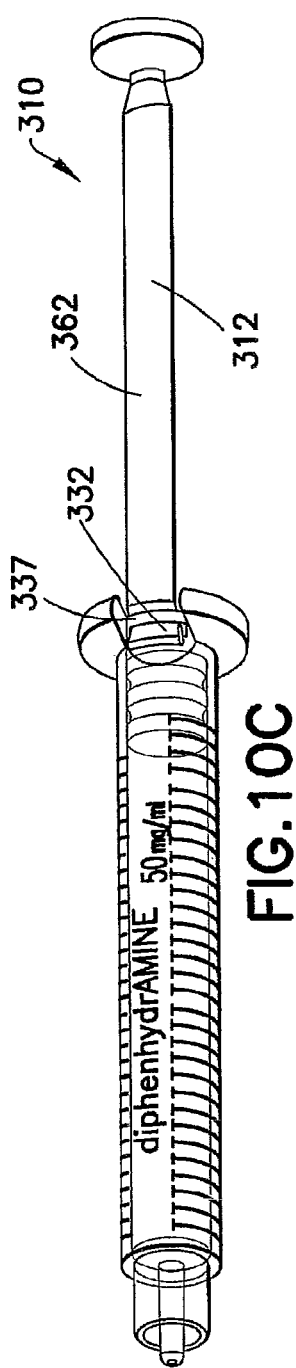
FIG. 10C is a perspective view of the syringe assembly of FIG. 10A having the plunger rod fully extended.
Figure 10D:
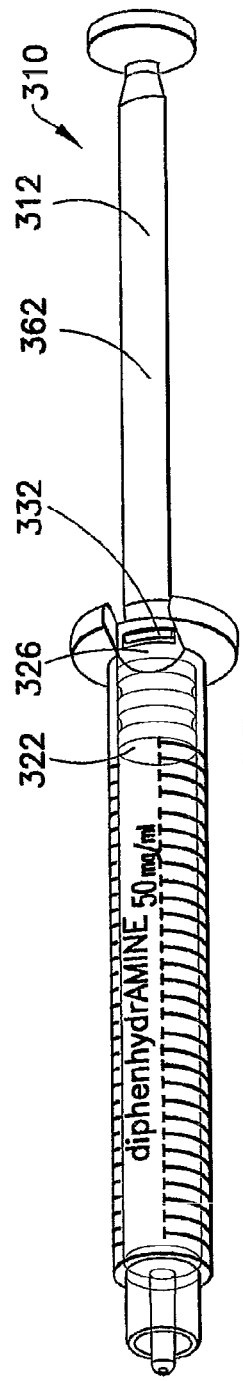
FIG. 10D is a perspective view of the syringe assembly of FIG. 10A in the ready-to-use position.
Figure 10E:
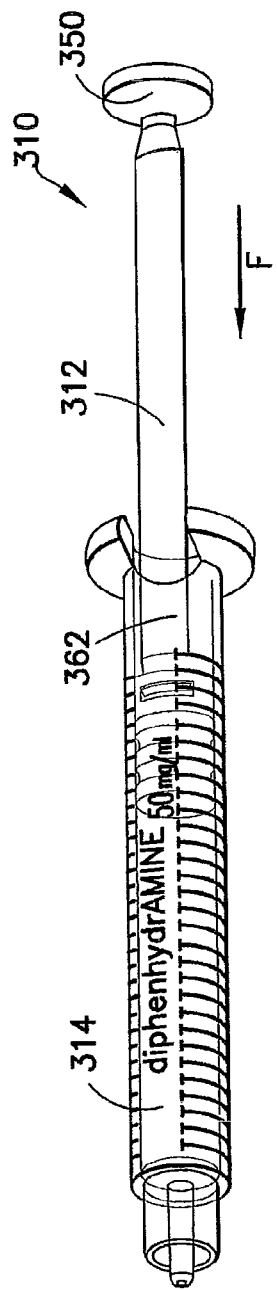
FIG. 10E is a perspective view of the syringe assembly of FIG. 10A having the plunger rod partially deployed to expel contents of the syringe barrel.

As shown in FIG. 10B, the plunger rod 312 may be pulled axially along the longitudinal axis $L_2$ of the syringe assembly 310 toward the proximal end 316 of the syringe barrel 314 and through cut-out portion 346. The fully extended plunger rod 312 is shown in FIG. 10C, having the attachment member 332 restrained by the containing member 337 to prevent separation of the plunger rod 312 from the syringe assembly 310. As shown in FIG. 10D, the attachment member 332 is engaged with the second end 326 of a stopper adapter to secure the plunger rod 312 with the stopper 322. As shown in FIG. 10E, the plunger rod 312 may be then deployed to expel the contents of the syringe barrel 314 by providing an axial force in the direction shown by arrow F to the thumb press member 350.

It can be appreciated that the collapsible plunger rod of the invention locks in place during use and can then be unlocked or unassembled to its initial position after use, where the plunger rod extends substantially parallel with and alongside and adjacent to the syringe body, to reduce the length of the syringe assembly to allow for sharps disposal. The use of the syringe assembly 310 having a collapsed plunger rod 312 of the invention can result in up to approximately a 70% reduction in length of the packaged syringe product.

While several embodiments of a syringe assembly that has a collapsible plunger rod were described in the foregoing detailed description, those skilled in the art may make modifications and alterations to these embodiments without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are embraced within their scope.

The invention claimed is:

1. A method of actuating a syringe assembly, comprising the steps of:
   providing the syringe assembly, comprising:
      a syringe barrel having an exterior surface, an inside surface defining a chamber, an open proximal end, a distal end, and an outlet disposed adjacent the distal end in fluid communication with the chamber; and
      a plunger assembly disposed at least partially within the syringe barrel, the plunger assembly including a plunger head and an elongated plunger rod having a first end and a second end, the elongated plunger rod being associated with the plunger head to move the plunger head within the chamber of the syringe barrel through an injection cycle,
      wherein the syringe barrel further includes at least one slot defined in the exterior surface between the open proximal end and the distal end and the plunger rod extends through the at least one slot and alongside at least a portion of the exterior surface of the syringe barrel in a collapsed position, said plunger rod being adapted to slidably move with respect to the syringe barrel;
   slidably withdrawing the plunger rod from the collapsed position to an extended position wherein at least a portion of the plunger rod remains in contact with the syringe assembly during transition from the collapsed position to the extended position;
   engaging the second end of the plunger rod with the plunger head to lock the plunger rod into engagement with the plunger head; and
   advancing the plunger assembly within the chamber of the syringe barrel so that the plunger head slides within the chamber with respect to the syringe barrel in a distal direction.

2. The method of claim 1, wherein the syringe barrel further includes an outwardly extending flange disposed at the open proximal end of the syringe barrel and at least one opening extending through the flange and wherein the plunger rod extends through the at least one opening.

3. The method of claim 1, wherein the plunger rod extends substantially parallel with the exterior surface of the syringe barrel in the collapsed position and extends substantially in line with a longitudinal axis of the syringe barrel in the extended position.

4. The method of claim 1, wherein the plunger rod includes an attachment member located at the second end.

5. The method of claim 4, wherein the attachment member on the plunger rod secures the plunger rod to the plunger head in the extended position.

6. The method of claim 1, wherein the plunger head includes a stopper having a proximal surface, a distal surface, and a peripheral surface extending between the proximal surface and the distal surface, the peripheral surface including at least one sealing surface for sealingly engaging the inside surface of the syringe barrel.

7. The method of claim 6, wherein the plunger head further includes a stopper adapter disposed on the proximal surface of the stopper, the stopper adapter being adapted to engage the plunger rod during the injection cycle.

8. The method of claim 7, further including a flange located at the proximal end of the syringe barrel, the flange including an opening in alignment with an opening in the stopper adapter through which the plunger rod extends wherein movement of the plunger rod from the collapsed position to the extended position includes pivoting the second end of the plunger rod in a radial direction with respect to the syringe barrel and then applying a proximal force to the plunger rod to axially slide the plunger rod through the openings in the flange and the stopper adapter and secure the second end of the plunger rod with the stopper adapter.

9. The method of claim 1, further including a cut-out portion in the proximal end of the syringe barrel and a containing member positioned adjacent the cut-out portion wherein said cut-out portion and said containing member are dimensioned to allow a portion of the plunger rod to pass therethrough but are dimensioned to prevent the first end and the second end of the plunger rod from passing through the cut-out portion to prevent inadvertent separation of the plunger rod from the plunger assembly.

10. The method of claim 1, wherein the plunger rod further includes an inwardly curved portion to facilitate manipulation of the plunger rod during transition from the collapsed position to the extended position.

11. The method of claim 1, wherein the plunger rod includes a thumb press member located at the first end of the plunger rod and located above the proximal end of the syringe barrel.

12. A method of actuating a syringe assembly, comprising the steps of:
providing the syringe assembly, comprising:
a syringe barrel having an exterior surface, an inside surface defining a chamber, an open proximal end, a distal end, and an outlet disposed adjacent the distal end in fluid communication with the chamber; and
a plunger assembly disposed at least partially within the syringe barrel, the plunger assembly including a plunger head and an elongated plunger rod having a first end and a second end, the elongated plunger rod being associated with the plunger head to move the plunger head within the chamber of the syringe barrel through an injection cycle,
wherein the syringe barrel further includes at least one slot defined in the exterior surface and the plunger rod extends through the at least one slot and alongside the exterior surface of the syringe barrel in a collapsed position, said plunger rod being adapted to slidably move with respect to the syringe barrel;
slidably withdrawing the plunger rod from the collapsed position to an extended position wherein at least a portion of the plunger rod remains in contact with the syringe assembly during transition from the collapsed position to the extended position;
engaging the second end of the plunger rod with the plunger head to lock the plunger rod into engagement with the plunger head; and
advancing the plunger assembly within the chamber of the syringe barrel so that the plunger head slides within the chamber with respect to the syringe barrel in a distal direction,
wherein the plunger head includes a stopper having a proximal surface, a distal surface, and a peripheral surface extending between the proximal surface and the distal surface, the peripheral surface including at least one sealing surface for sealingly engaging the inside surface of the syringe barrel,
wherein the plunger head further includes a stopper adapter disposed on the proximal surface of the stopper, the stopper adapter being adapted to engage the plunger rod during the injection cycle, and
wherein the syringe barrel further includes a flange located at the proximal end of the syringe barrel, the flange including an opening in alignment with an opening in the stopper adapter through which the plunger rod extends wherein movement of the plunger rod from the collapsed position to the extended position includes pivoting the second end of the plunger rod in a radial direction with respect to the syringe barrel and then applying a proximal force to the plunger rod to axially slide the plunger rod through the openings in the flange and the stopper adapter and secure the second end of the plunger rod with the stopper adapter.

* * * * *